United States Patent
Fujinuma et al.

(10) Patent No.: US 8,529,638 B2
(45) Date of Patent: Sep. 10, 2013

(54) HEAD HAIR DYEING COMPOSITION

(71) Applicant: Kao Corporation, Tokyo (JP)

(72) Inventors: Hiroyuki Fujinuma, Tokyo (JP); Takashi Matsuo, Tokyo (JP); Masahiko Ogawa, Tokyo (JP); Takeshi Iizaki, Tokyo (JP); Hiromi Saimiya, Tokyo (JP); Kazuhiro Okada, Tokyo (JP); Tomohito Koshika, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/762,981

(22) Filed: Feb. 8, 2013

(65) Prior Publication Data

US 2013/0185874 A1      Jul. 25, 2013

Related U.S. Application Data

(60) Division of application No. 13/107,183, filed on May 13, 2011, now Pat. No. 8,394,151, which is a continuation of application No. 12/739,835, filed as application No. PCT/JP2007/001160 on Oct. 24, 2007, now abandoned.

(51) Int. Cl.
*A61Q 5/10* (2006.01)
(52) U.S. Cl.
USPC ............. 8/405; 8/431; 8/457; 8/477; 8/526
(58) Field of Classification Search
USPC .............. 8/405, 431, 457, 477, 526
See application file for complete search history.

(56) References Cited

U.S. PATENT DOCUMENTS

| | | |
|---|---|---|
| 3,341,418 A | 9/1967 | Moses et al. |
| 3,709,437 A | 1/1973 | Wright |
| 4,823,985 A | 4/1989 | Grollier et al. |
| 4,961,925 A | 10/1990 | Tsujino et al. |
| 5,064,103 A | 11/1991 | Bennett |
| 5,143,518 A | 9/1992 | Madrange et al. |
| 5,651,793 A | 7/1997 | Hoeffkes et al. |
| 5,848,730 A | 12/1998 | Kawase et al. |
| 5,968,486 A | 10/1999 | Newell et al. |

(Continued)

FOREIGN PATENT DOCUMENTS

| | | |
|---|---|---|
| DE | 18 01 518 | 1/1971 |
| EP | 0 113 418 | 7/1984 |

(Continued)

OTHER PUBLICATIONS

"Make Your Hair Beautiful by Correct Usage—Hair Coloring ABC, revised edition." Feb. 1, 2000. pages 18-19. (with English translation).

(Continued)

*Primary Examiner* — Eisa Elhilo
(74) *Attorney, Agent, or Firm* — Foley & Lardner LLP

(57) ABSTRACT

There is provided a head hair dyeing method using a two-part hair dye composition which contains a first part containing an alkali agent, a second part containing hydrogen peroxide and a non-aerosol type foamer container for discharging a mixture solution of the first part and the second part as foam, the composition containing a surfactant in at least one of the first part and the second part, the method including discharging the mixture solution as foam, applying the foam to the head hair, and then re-foamed on the head hair.

18 Claims, 2 Drawing Sheets

(56) References Cited

U.S. PATENT DOCUMENTS

| | | | |
|---|---|---|---|
| 7,938,864 B2 | 5/2011 | Miyabe et al. | |
| 7,955,400 B2 | 6/2011 | Fujinuma et al. | |
| 8,002,848 B2 | 8/2011 | Miyabe | |
| 8,025,702 B2 | 9/2011 | Fujinuma et al. | |
| 8,025,703 B2 | 9/2011 | Ogawa et al. | |
| 2001/0039460 A1 | 11/2001 | Aisa | |
| 2004/0213752 A1* | 10/2004 | Fujinuma et al. | 424/70.1 |
| 2010/0126522 A1 | 5/2010 | Fujinuma et al. | |
| 2010/0126523 A1 | 5/2010 | Fujinuma et al. | |
| 2010/0236570 A1 | 9/2010 | Fujinuma et al. | |
| 2010/0242187 A1 | 9/2010 | Miyabe | |
| 2010/0251488 A1 | 10/2010 | Fujinuma et al. | |
| 2010/0257677 A1 | 10/2010 | Miyabe et al. | |
| 2010/0299848 A1 | 12/2010 | Fujinuma et al. | |
| 2010/0313905 A1 | 12/2010 | Fujinuma et al. | |
| 2010/0316583 A1 | 12/2010 | Fujinuma et al. | |
| 2011/0073128 A1 | 3/2011 | Ogawa et al. | |
| 2011/0214682 A1 | 9/2011 | Fujinuma et al. | |
| 2011/0277782 A1 | 11/2011 | Iijima et al. | |

FOREIGN PATENT DOCUMENTS

| | | |
|---|---|---|
| EP | 0 503 507 | 9/1992 |
| EP | 1 055 425 | 11/2000 |
| EP | 0 877 653 | 10/2002 |
| EP | 1 291 006 | 12/2003 |
| EP | 1 470 812 | 10/2004 |
| GB | 1 125 528 | 8/1968 |
| GB | 2 254 341 | 10/1992 |
| GB | 2 293 157 | 3/1996 |
| JP | 48-068750 | 9/1973 |
| JP | 55-049308 | 4/1980 |
| JP | 58-030282 | 6/1983 |
| JP | 59-108710 | 6/1984 |
| JP | 61-143412 | 7/1986 |
| JP | 62-242609 | 1/1987 |
| JP | 63-246313 | 10/1988 |
| JP | 04-099711 | 3/1992 |
| JP | 04-282307 | 10/1992 |
| JP | 04-282308 | 10/1992 |
| JP | 04-293568 | 10/1992 |
| JP | 2004-282308 | 10/1992 |
| JP | 06-107530 | 4/1994 |
| JP | 06-271435 | 9/1994 |
| JP | 07-023293 | 3/1995 |
| JP | 07-267834 | 10/1995 |
| JP | 07-330559 | 12/1995 |
| JP | 07-330560 | 12/1995 |
| JP | 08-040837 | 2/1996 |
| JP | 08-119838 | 5/1996 |
| JP | 08-119839 | 5/1996 |
| JP | 08-165235 | 6/1996 |
| JP | 08-199188 | 8/1996 |
| JP | 08-230959 | 9/1996 |
| JP | 08-231345 | 9/1996 |
| JP | 08-231346 | 9/1996 |
| JP | 08-259426 | 10/1996 |
| JP | 08-268848 | 10/1996 |
| JP | 08-283695 | 10/1996 |
| JP | 09-002923 | 1/1997 |
| JP | 09-002925 | 1/1997 |
| JP | 09-025223 | 1/1997 |
| JP | 02-579516 | 2/1997 |
| JP | 09-040534 | 2/1997 |
| JP | 09-136818 | 5/1997 |
| JP | 09-143040 | 6/1997 |
| JP | 09-506130 | 6/1997 |
| JP | 09-227347 | 9/1997 |
| JP | 09-234112 | 9/1997 |
| JP | 09-255541 | 9/1997 |
| JP | 09-301835 | 11/1997 |
| JP | 10-025230 | 1/1998 |
| JP | 10-167938 | 6/1998 |
| JP | 10-287534 | 10/1998 |
| JP | 10-324357 | 12/1998 |
| JP | 11-018836 | 1/1999 |
| JP | 11-018837 | 1/1999 |
| JP | 11-050089 | 2/1999 |
| JP | 11-124321 | 5/1999 |
| JP | 11-139945 | 5/1999 |
| JP | 11-199454 | 7/1999 |
| JP | 11-206454 | 8/1999 |
| JP | 11-246369 | 9/1999 |
| JP | 11-286421 | 10/1999 |
| JP | 01-349453 | 12/1999 |
| JP | 11-349453 | 12/1999 |
| JP | 2000-191471 | 7/2000 |
| JP | 2000-128215 | 9/2000 |
| JP | 2000-297018 | 10/2000 |
| JP | 2000-297019 | 10/2000 |
| JP | 2000-355527 | 12/2000 |
| JP | 2001-010930 | 1/2001 |
| JP | 2001-019626 | 1/2001 |
| JP | 2001-039460 | 2/2001 |
| JP | 2001-097834 | 4/2001 |
| JP | 2001-172166 | 6/2001 |
| JP | 2001-224649 | 8/2001 |
| JP | 2001-278742 | 10/2001 |
| JP | 2001-288054 | 10/2001 |
| JP | 2001-327321 | 11/2001 |
| JP | 2002-020247 | 1/2002 |
| JP | 2002-097121 | 4/2002 |
| JP | 2002-154938 | 5/2002 |
| JP | 2002-193771 | 7/2002 |
| JP | 2002-220329 | 8/2002 |
| JP | 2002-226340 | 8/2002 |
| JP | 2002-226344 A | 8/2002 |
| JP | 2002-284655 | 10/2002 |
| JP | 03-012479 | 1/2003 |
| JP | 2003-012479 | 1/2003 |
| JP | 2003-026554 | 1/2003 |
| JP | 2003-040747 | 2/2003 |
| JP | 2003-063936 | 3/2003 |
| JP | 2003-073240 | 3/2003 |
| JP | 2003-073241 | 3/2003 |
| JP | 2003-081791 A | 3/2003 |
| JP | 2003-095900 | 4/2003 |
| JP | 2004-339216 | 12/2004 |
| JP | 2006-124279 | 5/2006 |
| JP | 2007-119480 | 5/2007 |
| JP | A01-002007 | 11/2007 |
| JP | 2007-314523 A1 | 12/2007 |
| JP | 2010-006803 | 1/2010 |
| JP | 2010-006805 | 1/2010 |
| WO | WO-91/14759 | 10/1991 |
| WO | WO-95/16023 | 6/1995 |
| WO | WO-00/76468 | 12/2000 |
| WO | WO-01/85105 | 11/2001 |
| WO | WO-01/85113 | 11/2001 |
| WO | WO-2007/007936 | 1/2007 |

OTHER PUBLICATIONS

371-EPO Response in European Patent Application No. 04009836.0, Jul. 15, 2011.
Amendment filed Dec. 5, 2008 in European Patent application No. 0 400 9836.0.
Amendment filed Sep. 10, 2010 in Japanese application No. 2004-130373 (w/ English Translation).
Amendments to the Claims in Japanese Patent Application No. 2010-268209, filed on Apr. 8, 2011. (with English translation).
Analysis Methods for Surfactants. Oct. 1, 1975. pp. 117-118. (with English translation).
Analytical Chemistry Handbook, revised second edtion. Oct. 10, 1971. pp. 27-29. (with English translation).
Arai, Yasuhiro. "State-of-the art: Hair Color Technology—Trends in development as seen in patents." Published by Fragrance Journal Ltd. Aug. 25, 2004. pp. 102-105, 212-213. (with English translation).
Chemical Daily. "Surfactant—Remarkable performance of nonionic surfactant (Market conditions in chemicals)." Jan. 25, 2002. (with English translation).
Chemical Daily. "Surfactant—Started growing responding to sety requirement." Jan. 19, 2000. (with English translation).

Chemical Daily. "Surfactant—Penetrated to the various fields taking advantage of unique characteristics." Jan. 21, 1999. (with English translation).
Close-up photocopy of the folding, collapsible box for "Poly Brillance Intensiv-Color-Crème" Aug. 25, 1997.
Communication Pursuant to Article 94(3) EPC issued Dec. 29, 2008 in European Patent application No. 0 400 9836.0.
Communication Pursuant to Article 94(3) EPC issued Jun. 28, 2010 in European Patent application No. 0 400 9836.0.
Communication Pursuant to Article 94(3) EPC issued Nov. 5, 2010 in European Patent application No. 0 400 9836.0.
Comprehensible Surfactant, first edition. Sep. 1, 2003. pp. 32-49. (with English translation).
Comprehensive Dictionary of Chemistry. Oct. 20, 1989. pp. 56, 60-61, 646-647, 1762-1763. (with English translation).
Corresponding application filed in Japanese Application No. 2004-130373, filed on Nov. 10, 2008.
Cosmetics Dictionary, first edition. Oct. 1, 1992. p. 373. (with English translation).
Cosmetics Handbook. Nov. 1, 1996. pp. 220-221, 441-444. (with English translation).
Decision of Refusal issued Jun. 16, 2010 in Japanese application No. 2004-130373 (w/ English Translation).
Decision to Refuse a European Patent Application issued Apr. 19, 2011, in regard to European Patent Application No. 087512171.2, filed Apr. 25, 2008.
Declaration by Akiko Nagabuchi (with English translation), served on Sep. 21, 2011, in regard to No. 22009, 2011 (yo).
Declaration by Hattori, Nobuhito, in regard to No. 22056, 2011 (yo), served on Dec. 28, 2011 (with English translation).
Denavarre, Maison G. The Chemistry and Manufacture of Cosmetics, second edition, vol. 4. 1975. pp. 841-863.
Dr. Matthias Schweinsberg, Test Report : Foaming Characteristics and Flow Characteristics of Cosmetic Products According to EP 1 291 006 Al, Feb. 17, 2012 with English Translation, served on Apr. 17, 2012 in regard to DE litigation No. 4a 028/11.
English translation of Amendment filed Mar. 9, 2009 in Japanese application No. 2004-130373.
English Translation of Decision to Grant a Patent issued Jan. 4, 2011 in Japanese Patent application No. 2004-130373 w/ Allowed Claims.
English Translation of Decision to Grant a Patent issued Jan. 4, 2011 in Japanese Patent application No. 2008-270377 w/ Allowed Claims.
English translation of Notification of Reasons for Refusal issued Jan. 6, 2009 in Japanese application No. 2004-130373.
English translation of Notification of Reasons for Refusal issued Jul. 22, 2008, in Japanese Application No. 2004-130373.
English translation of Remarks filed Mar. 9, 2009 in Japanese application No. 2004-130373.
English translation of Remarks filed Oct. 20, 2008 in Japanese application No. 2004-130373.
English translation of Submission of Publication and the like, dated Dec. 25, 2007, in Japanese Patent Application No. 2004-130373.
English translation of Submission of Publication and the like, dated Feb. 29, 2008, in Japanese Patent Application No. 2004-130373.
English translation of Submission of Publications and the like, filed Mar. 24, 2009, in Japanese Application No. 2004-130373.
English translation of Submission of Publications and the like, filed Nov. 10, 2008, in Japanese Application No. 2004-130373.
English translation of Submission of Publications and the like, filed Sep. 7, 2009, in Japanese Application No. 2004-130373.
English translation of Submission of Publications filed Dec. 25, 2007 in Japanese application No. 2004-130373.
English translation of Submission of Publications filed Feb. 29, 2008 in Japanese application No. 2004-130373.
English translation of Submission of Publications filed Nov. 10, 2008 in Japanese application No. 2004-130373.
Entire contents of the folding, collapsible box for "Poly Brillance intensiv-Color-Crème" Aug. 25, 1997.
European Patent Office Communication issued Mar. 12, 2012 in European Patent Application 04 009 836.0.
European Patent Office Communication pursuant to Rule 114(2) EPC issued May 3, 2011, in European Application No. 04009836.0 filed Apr. 26, 2004.

European Search Report submitted Aug. 23, 2004, in European Patent Application No. 04009836.0.
Excerpt from the Internet Website: www.bagonvalve.com in regard to Request Cancelation in Utility Model 20 2004 021 775, served on Apr. 18, 2012, (3 pp.).
Experiment Result Report 1 (with English translation), prepared on Jul. 11, 2011, in regard to No. 22009, 2011 (yo).
Experiment Result Report 5 (with English translation), served on Sep. 21, 2011, in regard to No. 22009, 2011 (yo).
Experimental Report 1 (with English translation), served on May 24, 2011, in regard to Heisei 23 year (Yo) No. 22009.
Experimental Report 3 (with English translation), served on May 25, 2011, in regard to Heisei 23 year (Yo) No. 22009.
Experimental Result Report 13 (with English translation), served on Jan. 30, 2012, in regard to No. 22009, 2011 (yo).
Experimental Result Report 2 (with English translation), prepared on Jul. 22, 2011, in regard to No. 22009, 2011 (yo).
Experimental Result Report 6 (with English translation), served on Sep. 21, 2011, in regard to No. 22009, 2011 (yo).
Experimental Result Report 7 (with English translation), served on Sep. 21, 2011, in regard to No. 22009, 2011 (yo).
Experimental Result Report 8 (with English translation), served on Nov. 29, 2011, in regard to No. 22009, 2011 (yo).
Extended European Search Report issued Apr. 7, 2011, in European Application No. 10183376.2.
Extended European Search Report issued in Nov. 4, 2010 in European Patent Application No. 10172766.7.
Feminine Treatment Hair Color 84, Certification for Approval for Manufacture of Quasi-Drug (with English Translation), Jan. 30, 1997.
Food and Packaging. vol. 34, No. 8. "Can Technology Study Group." Aug. 1, 1993. 6 pages.
Fragrance Journal. vol. 19, No. 6. "Recent Progress of Hair Dyes and Problems in Research and Development." Jun. 15, 1991. pp. 26-27. (with English translation).
Hair Mode. Aug. 1996. No. 437, p. 108. (with partial English translation).
Handbook—Raw Materials of Cosmetics and Drugs—revised edition. Feb. 1, 1977. pp. 358 361. (with English translation).
Handbook "Poly Haarberater Coloration," original edition, 1992. pp. 76-77.
Hayakawa, Masakatsu. Fragrance Journal. "Trends in the R&D of Hair Dyes and Issues to Address." No. 38 (vol. 7, No. 5) Sep. 25, 1979. pp. 41-44. (with English translation).
Henkel Study Report, Study No. 1100546-1. "Open Epicutaneous Test," served on Jan. 30, 2012, in regard to No. 22009, 2011 (yo).
Henkel Study Report, Study No. 1100546-2. "Single Application Epicutaneous Patch Text (24th Patch Test)," served on Jan. 30, 2012, in regard to No. 22009, 2011 (yo).
Instructions for Feminine Retouch Color (with English Translation), Feminine Co., Ltd., published before Apr. 23, 2003. (served on May 25, 2011, in regard to Heisei 23 year (Yo) No. 22009).
Instructions for use contained in the folding, collapsible box for "Poly Brillance Intensiv-Color-Crème" Aug. 25, 1997.
Ishikawa, Ryoji. Experimental Report, in regard to No. 22056, 2011 (yo). Dec. 28, 2011 (with English translation).
Iwakura, Ryouhei, "Present State and Problems of Hair Dyes," Fragrance Journal, Special Issue. No. 11, pp. 87-93. Dec. 25, 1993. (with English Translation).
Japanese Collection of General Raw Materials for Cosmetics, fourth edition. Oct. 31, 1997. p. 583. (with English translation).
Japanese Patent Office Communication. Apr. 21, 2009, 3 pp. (includes statement submitted by third party).
Kishi, Haruo. Modern Fragrance and Cosmetics Science, 1st Edition. Mar. 20, 1979. pp. 42-47. (with English translation).
Mitsui, Takeo. New Cosmetic Science. Jan. 12, 1993. pp. 137-142. (with English translation).
Miyagi, Takashi. Food and Container, vol. 35, No. 10. pp. 588-593. (with English translation), (1994).
Miyagi, Takashi. Food and Container, vol. 35, No. 11. pp. 624-627. (with English translation), (1994).

Miyagi, Takashi. Food and Packaging, vol. 34, No. 8. "Does Non-Gas Container Cause a Boom? (Part 2)" 1993. pp. 467-471. (with English translation).
Miyagi, Takashi. Food and Packaging, vol. 34, No. 9. "Will Non-Gas Containers Create a Boom? (No. 3)" 1993. pp. 531-535. (with English translation).
Miyagi, Takashi. Food and Packaging, vol. 36, No. 3. Non-Gas Container Having Increased Level of Accomplishment (Part 3). 1995, pp. 154-158. (with English translation).
Miyagi, Takashi. Food and Packaging, vol. 42, No. 10. "Growing Pump Foamer Spreading into Western Markets, Part One: Mini-Foamer." Oct. 1, 2001. pp. 609-613. (with English translation).
Mottram, F.J., et al. Poucher's Perfumes, Cosmetics and Soaps, 10th ed. © 2000. "Hair Shampoos." pp. 295-301.
Murata, Seishiro. Cosmetic Dictionary, 1st edition. pp. 182-183, 666-667. Dec. 15, 2003. (with English translation).
Nakanishi, Fumio, et al. Science History of Hair Dye. Jan. 8, 1991. pp. 45-47. (with English translation).
Nakanishi, Fumio. Fragrance Journal. "Function of Recent Hair Coloring Agent and Developmental Trend Thereof." Aug. 15, 2001. pp. 39-45. (with English translation).
Nakanishi, Fumio. Fragrance Journal. "Recent Progress and Prospective Problems in Hair Colorants and Hair Lighteners" vol. 25, No. 1. Jan. 15, 1997. pp. 49-56. (with English translation).
New Cosmetic Science, second edition. Jan. 18, 2001. pp. 152-153. (with English translation).
Non-Final Office Action U.S. Appl. No. 13/107,183 dated Jun. 28, 2011.
Notice of Allowance U.S. Appl. No. 13/107,183 dated Jan. 10, 2012.
Notice of Allowance U.S. Appl. No. 13/107,183 dated Apr. 20, 2012.
Notice of Allowance U.S. Appl. No. 13/107,183 dated Dec. 10, 2012.
Notice of Allowance U.S. Appl. No. 13/107,183 dated Jan. 14, 2013.
Notice of Allowance U.S. Appl. No. 13/107,183 dated Jul. 30, 2012.
Notification of Reason for Refusal, dated Jul. 22, 2008, in Japanese Patent Application No. 2004-130373.
Notification of Third Office Action Chinese Application No. 200780100733.0 dated Oct. 9, 2012.
Observations under Rule 114(2) EPC filed Apr. 9, 2010 in European Patent application No. 0 400 9836.0.
Office Action issued Jun. 15, 2011 in corresponding Chinese Application No. 200780100733.0 (w/English translation).
Office Action issued Nov. 5, 2010, in EP Application No. 04 009 836.0.
Omura, Takayuki, et al. Fragrance Journal. "Development Trend and Problems of Recent Hair Foam." Mar. 15, 1994. pp. 29-35. (with English translation).
Pharmaceutical Additive Dictionary, 2nd edition. pp. 153-154, 203-205. Mar. 25, 2005. (with English Translation).
Photocopy a folding, collapsible box for "Poly Brillance Intensiv-Color-Creme", dated as Aug. 25, 1997.
Prettia Product Information (with English Translation), Kao Corporation, published after Apr. 23, 2003. (served on May 25, 2011 in regard to Heisei 23 year (Yo) No. 22009).
Publication of Unexamined Patent Application JP 2003-81369, Mar. 19, 2003.
Quasi Drugs Manufacturing Material Specification 2006, first edition. pp. 527-528. Jun. 16, 2006. (with English translation).
Remarks filed Feb. 25, 2011 in European Patent application No. 08 752 171.2.
Reply to EESR in European Patent Application No. 10172766.7, Apr. 29, 2011.
Response to Communication filed Aug. 10, 2010 in European Patent application No. 0 400 9836.0.
Response to Communication filed Feb. 18, 2011 in European Patent application No. 0 400 9836.0.
Response to Communication filed Jul. 8, 2009 in European Patent application No. 0 400 9836.0.
Response to Communication Pursuant to Article 96(2) EPC filed Apr. 25, 2007 in European Patent application No. 0 400 9836.0.
Robbins, Clarence R. "Chemical and Physical Behavior of Human Hair, fourth edition." Jul. 10, 2006. pp. 221-231. (with English translation).
Rompps Chemie Lexikon, vol. 6, 8th Ed. 1998. p. 4531.

Sato, Takatoshi, et al. Fragrance and Cosmetics Science. Mar. 20, 1997. pp. 73-74. (with English translation).
Sato, Takatoshi, et al. Fragrance Journal. "Future View of Hair Care Products." Jan. 15, 1997. pp. 49-56. (with English Translation).
Sato, Takatoshi. Science of Cosmetics. Mar. 20, 1997. pp. 138-140. (with English translation).
Shinbiyo Marcel. Oct. 1996. No. 31, pp. 73 and 83. Vivid Highlight advertisement page (with English Translation).
Study Report, No. 1100547-1. "Dermatological Use Test with Hair-Coloring Products in Split Design," served on Jan. 30, 2012, in regard to No. 220009, 2011 (yo).
Submission of Publications and the like, dated Mar. 24, 2009, in Japanese Patent Application No. 2004-130373, (with English translation).
Submission of Publications and the like, dated Nov. 10, 2008, in Japanese Patent Application No. 2004-130373.
Submission of Publications and the like, filed Apr. 8, 2009 in Japanese application No. 2004-130373 (w/ English Translation).
Submission of Publications and the like, filed Oct. 18, 2010 in Japanese application No. 2004-130373 (w/ English Translation).
Submission of Publications and the like, filed Oct. 25, 2010 in Japanese application No. 2008-270377 (w/ English Translation).
Tashima, Masaru, et al. Fragrance Journal. "Research and Development of Mist Foam Type Hair Styling Product." Dec. 15, 1992. pp. 61-69. (with English translation).
Taya-A.T. HM Education Mook., Series 3. "Knowing Mechanisms of Hair Coloring Agents." Apr. 10, 1998. pp. 8-9. (with English translation).
Test Report 4 (with English translation), served on Jul. 10, 2011, in regard to Heisei 23 year (Yo) No. 22009.
Test Report dated May 1, 2012, Hoyu Co., Ltd., Product Development Laboratory of General Research & Development Institute, Section Chief: Ryouji Ishikawa, served on May 11, 2012 in regard to No. 5260, 2012 (wa) with English translation, (13 pp.).
The Handbook of Oil Chemistry, 4th ed. "Lipids and Surfactants." Nov. 20, 2001. p. 522. (with English translation).
The Nikkan Kogyo Shimbun, Ltd. "Nonylphenol Identified as Endocrine Disrupting Chemical." Aug. 6, 2001. (with English translation).
Third Party Observation filed on Apr. 27, 2011, in European Patent Application No. 0 400 9836.0 (including translation of submission).
Third-Party Observation filed on Dec. 19, 2009 in European Patent application No. 0 400 9836.0.
Third Party Observation filed on May 10, 2010 in European Patent application No. 0 400 9836.0.
Third-Party Observation submitted Jun. 24, 2011, in European Patent Application No. 10172766.7.
Third Party Observation submitted Jun. 24, 2011, in European Patent Application No. 10183376.2.
Third-Party Observation submitted Jun. 3, 2011, in European Patent Application No. 10172766.7, filed Apr. 26, 2004.
Third-Party Observation submitted May 12, 2011, in European Patent Application No. 04009836.0.
Third-Party Observation submitted May 3, 2011, in European Patent Application No. 0 400 9836.0.
Unichemy Corp. Experimental Report, in regard to No. 22056, 2011 (yo). Issued on Jun. 24, 2011 (with English translation).
US Notice of Allowance DTD Jul. 16, 2012.
Vivid Highlight. Iriya Cosmetics. Packaging and Instructions Insert. Sep. 6, 1996 (with English translation).
Watanabe, Yasushi, et al. Hair Science. "Hair Colorant." Feb. 1, 1986. pp. 144-150. (with English translation).
Written Argument filed by the Debtor (1/2) in the Case of Request for Provisional Disposition of Patent Right: No. 22056, 2011 (yo), served on Sep. 6, 2011. pp. 1-5, 29-34. (with partial English translation).
Written Demand for Appeal filed Sep. 10, 2010 in Japanese application No. 2004-130373 (w/ English Translation).
Yamagata, Yoshifumi, et al. Fragrance Journal. "Science of Foam: Function and Physical Properties of Foam." Dec. 15, 1992. pp. 37-47. (with English translation).
Yamakawa, Arata, et al. Fragrance Journal. "Development and Objective of Mousse Hair Cosmetic Products." Dec. 15, 1992. pp. 48-54. (with English translation).

Yasuda, Kosaku, et al. Knowledge of Fat and Oil Products. Aug. 25, 1977. pp. 240-244. (with English translation).

Packaging and Instructions Insert of VENEZEL (Dariya Corporation).

Mitsui, Takeo. New Cosmetic Science, second edition. Jan. 18, 2001. pp. 470-475.

* cited by examiner

HEAD HAIR DYEING COMPOSITION

CROSS-REFERENCE TO RELATED APPLICATIONS

The present application is a divisional application of U.S. Ser. No. 13/107,183, filed May 13, 2011 now U.S. Pat. No. 8,394,151 B2, which is a continuation application of U.S. Ser. No. 12/739,835, filed on Apr. 26, 2010 now abandoned, which is the U.S. National Stage of PCT/JP07/01160, filed Oct. 24, 2007. Each of which is incorporated in entirety by reference.

FIELD OF THE INVENTION

The present invention relates to a head hair dyeing method using a two-part hair dye composition.

BACKGROUND OF THE INVENTION

While liquid or creamy hair dye compositions have been widely used so far, it is difficult to apply these compositions to the head hair evenly. In particular, in the case of consumers themselves applying a hair dye composition to their own head hair at the roots or on the back of the head, they need to acquire skills of, such as, "blocking" or using two mirrors facing each other ("two-mirror technique"), and a careful operation is required to apply the composition evenly.

Accordingly, discharging a composition as foam in order to simplify the hair dyeing operation has been proposed, and hair dyes of a two-part aerosol type and those of a one-part non-aerosol type are known, for example. However, those of a two-part aerosol type have such problems that uneven bleaching or uneven dyeing is likely to occur due to an inconsistent mixing ratio of a first part and a second part, a pressure-proof metal container or the like is oxidized and corroded by hydrogen peroxide, and the internal pressure of the pressure-tight container is excessively increased by degradation of hydrogen peroxide. Furthermore, since such a one-part non-aerosol type has no or weak bleaching ability, it is difficult to achieve a great change in the color tone by one procedure. Therefore, a problem arises, i.e., a hair dyeing operation tends to be cumbersome since a hair dye is required to be left to develop for a long time and the procedure is required to be repeated after application.

On the other hand, discharging a two-part hair dye composition as foam from a non-aerosol type foamer container (e.g., Patent Documents 1 and 2) has been proposed. By discharging a mixture solution of a first part and a second part from a foamer container as foam, variation in the mixing ratio hardly occurs compared to conventional two-part aerosol hair dyes and a sufficient bleaching or hair dyeing ability may be obtained compared to conventional one-part non-aerosol hair dyes.

Meanwhile, all of these two-part aerosol type hair dyes, one-part non-aerosol hair dyes and two-part non-aerosol hair dyes, by which the hair dyes are discharged as foam from foamer containers, still suffer a common problem, i.e., it is difficult to adjust foam quality by which easiness of discharging from a container and operatability on the head hair are well-balanced. To solve this problem, for example, Patent Document 3 proposes a composition that maintains adequate foam quality and has an excellent foam breaking property at the time of application to the hair. However, a careful operation is still required for even application, and an alternative dyeing method has been needed.

[Patent Document 1] JP-A-2004-339216
[Patent Document 2] JP-A-2006-124279
[Patent Document 3] JP-A-2001-019626

SUMMARY OF THE INVENTION

The present invention provides a head hair dyeing method using a two-part hair dye composition which contains a first part containing an alkali agent, a second part containing hydrogen peroxide and a non-aerosol type foamer container for discharging a mixture solution of the first part and the second part as foam, at least one of the first and second parts containing a surfactant, the method including discharging the mixture solution as foam, applying the mixture solution to the head hair, and then re-foaming the mixture solution on the head hair.

Figure 1:
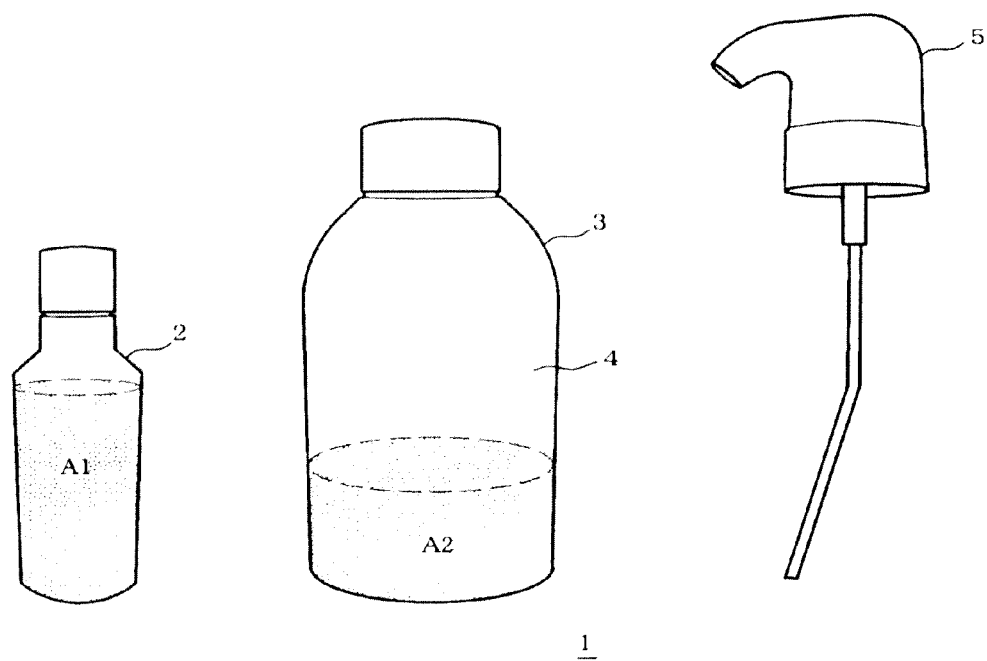
FIG. 1 shows a state of the two-part hair dye composition used in the examples and the comparative examples before mixing.

| | |
|---|---|
| 1 | Units of two-part hair dye composition |
| 2 | First container |
| 3 | Second container |
| 4 | Body of Squeeze container |
| 5 | Squeeze foamer |
| 6 | Squeeze container |
| A1 | First part |
| A2 | Second part |
| A3 | Mixture |

DETAILED DESCRIPTION OF THE INVENTION

Viscosity of a mixture solution is required to be made low in order to form foam with a non-aerosol type foamer container. However, depending on the property of formed foam, foam may disappear during application or leaving out, and the mixture solution applied to the head hair easily drips down due to the low viscosity.

Furthermore, while it is so convenient that any skills such as blocking and two-mirror technique are not required, however, a high defoaming rate inhibits visualization of incomplete or uneven application to the hair in back of the head. Therefore, uneven hair dyeing may occur, the reason of which is different from those in the use of liquid or creamy hair dyes.

The present invention relates to a head hair dyeing method, by which a two-part hair dye composition, foamed by using a non-aerosol type foamer container, does not drip down between the applying to the head hair and the rinsing off, and incomplete or uneven application is avoided.

The inventors of the present invention found a head hair dyeing method that satisfy the above-described requirements, the method including applying a two-part hair dye composition discharged as foam on the head hair by using a non-aerosol type foamer container and the two-part hair dye composition and re-foaming the applied foam on the head hair thereafter.

According to the present invention, since the applied foam is re-foamed on the head hair, foam of a two-part hair dye composition can be rapidly and reliably spread over to the roots of the head hair without blocking, even the hair in back of the head, a part which is difficult to check, while avoiding incomplete or uneven application without using mirrors. In addition, dripping can be prevented irrespective of the foam property that may be varied depending on the structure of a foamer container or the composition of a two-part hair dye composition.

[Head Hair Dyeing Procedures]
[Definition]

In the present invention, the head hair refers to the hair grown on the head, and the concept thereof does not include the hair separate from the head such as a wig and a tress. Furthermore, the head hair may be the hair of a doll or any animal, but human head hair is preferred.

In the head hair dyeing method of the present invention, a two-part hair dye composition including a first part containing an alkali agent and a second part containing hydrogen peroxide is used, in which a surfactant is contained in at least one of the first part and the second part. In the present invention, the two-part hair dye composition is a concept including both a hair dye composition that contains a dyestuff and a bleach composition that does not contain a dye. The head hair dyeing method is a concept including a head hair bleaching method.

[Mixture of First Part and Second Part]

A two-part hair dye composition is used for hair dyeing treatment by mixing a first part and a second part immediately before use. In the present invention, the first part and the second part may be mixed by any of the following procedures:

1) Mixing before filling in the main body of a foamer container;

2) Mixing in the main body of a foamer container;

3) Mixing by joining the first part and the second part together in a gas-liquid mixing chamber of a foamer;

4) Once foaming the first part and the second part separately and then mixing by joining them together before discharging from the foamer;

5) Mixing separately discharged foams of the first part and the second part before applying to the head hair; or 6) Mixing separately discharged foams of the first part and the second part on the head hair.

Of these, the procedures of 1) mixing before filling in the main body of the foamer container and 2) mixing in the main body of the foamer container are preferred, from viewpoints that the structure of the foamer container can be simplified, compositions of the first part and the second part can be freely designed, and a reliable uniform mixture can be obtained.

[Non-Aerosol Type Foamer Container]

In the present invention, the foamer container is a non-aerosol type container and is used to mix a first part and a second part or a mixture solution thereof with air and discharge them as foam without using a propellant. Use of the foamer container can also prevent the discharged compositions from spattering. In particular, a non-aerosol type container can be manufactured at low costs than an aerosol type container, the discharging rate can be easily adjusted, the container can be re-used by performing a certain treatment, and products can be handled more safely during distribution since no high-pressure gas propellant is required.

Any container may be used as the foamer container so long as it is a non-aerosol type container having a foam discharging means such as a known pump foamer container or squeeze foamer container having a foam discharging means.

The pump foamer container or the squeeze foamer container has a foam generating portion such as a net, and preferably has a thin net, from a viewpoint that, when a mixture solution of the first part and the second part is solidified to dryness causing clogging, the solids can be immediately dissolved by the flow of foam at the next discharge, resulting in resolution of clogging. In this case, the net preferably has a 50 to 280 mesh, more preferably a 90 to 250 mesh, and even more preferably a 130 to 220 mesh. Creamy foam can be produced by using a net mesh in this range. Furthermore, preferred examples of materials of such a mesh include nylon, polyethylene, polypropylene, polyester, teflon (registered trade name), carbon fiber, stainless, and so forth. Of these, nylon, polyethylene, polypropylene, and polyester are more preferred, and nylon is even more preferred.

In the foamer container used in the present invention, at least one, preferably two or more of such nets are disposed. More preferably, two nets are disposed from viewpoints of economic efficiency, foam stability, and the like. In this case, a mesh through which the solution passes first is preferably as coarse as or coarser than a mesh through which the solution passes next.

In the foamer container, a portion in contact with the contents (e.g., inner wall of a container, inner wall of a foam discharging means, etc.) is preferably constituted by materials that are not corroded by alkalis or hydrogen peroxide and are able to pass oxygen generated by degradation of hydrogen peroxide.

As a product form of the two-part hair dye composition used in the present invention containing a first part, a second part and a foamer container, the first part and the second part may be filled in respective containers separate from the foamer container, so that both the parts should be transferred to the foamer container and mixed before use. Alternatively, one part may be filled in the foamer container, and the other part may be filled in a separate container, so that the other part should be transferred into the foamer container before use. In this case, the second part is preferably filled in a foamer container composed of a container having gas permeability to prevent the increase of a pressure in the container due to oxygen generated by degradation of hydrogen peroxide, and more preferably filled in a foamer container made of a material having oxygen permeability (e.g., polypropylene or polyethylene). On the other hand, a container that hardly passes oxygen is required to be used for the first part to prevent oxidation of an oxidative dye.

[Specific Procedures]

In the head hair dyeing method of the present invention, it is preferable to comb the head hair in advance of application of discharged foam. Consequently, the hair hardly gets tangled during the re-foaming treatment, so that the hair dye composition is not likely to splatter. Furthermore, after the head hair is combed, blocking, generally performed in application of a hair dye composition, is not required, and it is preferable not to perform blocking. Consequently, the hair dye composition is easily applied to the head hair or re-foamed as described later.

From viewpoints of even hair dyeing, prevention of dripping, and a sufficient hair dyeing effect, it is preferable that hair dressing is not applied to the head hair to which the hair dye composition is to be applied immediately before the hair dyeing. Furthermore, from viewpoints that the mixture solution is not diluted even hair dyeing can be provided, dripping may be prevented and a sufficient hair dyeing effect may be obtained, dry head hair is preferred. When the hair is washed immediately before the hair dyeing treatment, it is preferable to dry the head hair before hair dyeing treatment. Drying the head hair means that the liquid, mainly water, attached due to the hair wash is removed at least to the extent that it does not drip in a spontaneous state. Specifically, it is preferable to dry the hair with a towel or a dryer.

The mixture solution of the first part and the second part discharged as foam is applied to the head hair after placing it on the hands or a brush, or directly. Here, when hands are used, it is preferable to wear gloves. According to the dyeing method of the present invention, since blocking generally performed in the application of a hair dye composition is not required, the foam may be applied in a short time. Therefore, the application of foam may be started at any head hair site, and it is not necessary to apply it starting with the neckline unlike conventional liquid or creamy two-part hair dye compositions. It is sufficient to start the application at a concerned portion, and it is preferable to apply foam from the hairline of the head hair or a site where the hair is parted.

It is preferable to discharge foam in about the size of a lemon because it is the proper size to place on one hand and to easily apply to the head hair using hands. In this case, foam is discharged with one hand and received with the other hand. Then, after foam received on the hand is once applied to the head hair, foam is discharged on the hand again to repeat the application to the head hair. This series of operations may be performed very conveniently in a short period.

Furthermore, foam may be applied to the whole head hair or only a specific portion.

Then, the applied foam is re-foamed on the head hair. The foam may be re-foamed by injecting a gas, using an instrument such as a vibrator or a brush, or with fingers. However, since the two-part hair dye composition may be thoroughly spread to the roots of the head hair, it is more preferable to use fingers. The rate of foaming using a vibrator or a brush or with fingers is preferably controlled so that the foam should not spatter.

Here, the timing of re-foaming may be after the foam has disappeared completely, during the process of disappearance, or before the applied foam changes. Alternatively, the timing may be after the foam has been completely applied to the area that needs applying the foam or during the process of application. Re-foaming may be performed continuously once or intermittently in several times. Here, when a vibrator, a brush, or fingers used for re-foaming remain in contact with a part of the head hair, or they are brought into contact within 1 second even if they are once separated, the re-foaming is assumed as continuous. In short, it is sufficient to observe the applied site and suitably foam at least before liquid drips from the applied foam. Irrespective of the property of the foam, dripping may be prevented by re-foaming the foam that almost disappears. Furthermore, by re-foaming, foam may be changed to the quality suitable for hair dyeing regardless of differences in the structure of the foamer container or the property of the foam depending on the composition of the two-part hair dye composition. In some cases, dripping may be prevented, and the foam quality suitable for hair dyeing may be maintained as it is by using a specific structure of the foamer container or a specific composition of the two-part hair dye composition. Even in such cases, however, it is preferable to perform re-foaming at least once as early as possible after the completion of the foam application. By performing re-foaming at an early stage, uneven coloring in an area that needs applying may be prevented. This timing is preferably within 5 minutes after the completion of application of the discharged foam to the head hair, more preferably within 3 minutes, even more preferably within 1 minute.

Hereafter, specific examples of preferred procedures in the processes from discharge of foam to application to the head hair and re-foaming will be shown according to partial hair dyeing and whole head hair dyeing.

[Partial Hair Dyeing]

1) Discharge a suitable amount of foam on one hand, apply the foam to a part of the head hair, and perform one operation of re-foaming over 1 second to 10 minutes, preferably 3 seconds to 3 minutes.

2) Discharge a suitable amount of foam on one hand, apply the foam to a part of the head hair, perform one operation of re-foaming over 1 second to 10 minutes, preferably 3 seconds to 3 minutes, and repeat the operation 2 to 30 times. Re-foaming is performed over a total of 2 seconds to 20 minutes, preferably 5 seconds to 5 minutes.

[Whole Head Hair Dyeing]

3) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head.

4) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head, and then perform one operation of re-foaming over 3 seconds to 10 minutes, preferably 5 seconds to 3 minutes. Further, discharge a suitable amount of foam on one hand, additionally apply the foam to a part of the head hair, and perform one operation of re-foaming over the whole head over 3 seconds to 10 minutes, preferably 5 seconds to 3 minutes.

5) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head. After completion of the application to the whole head, perform one operation of re-foaming over 3 seconds to 10 minutes, preferably 5 seconds to 5 minutes.

6) Discharge a suitable amount of foam on one hand, apply the foam to a part of the head hair, and perform one operation of re-foaming over 3 seconds to 10 minutes, preferably 5 seconds to 3 minutes. Repeat this operation to apply the foam over the whole head. After completion of the application to the whole head, perform one operation of re-foaming over the whole head over 3 seconds to 10 minutes, preferably 5 seconds to 3 minutes, and repeat the operation 2 to 30 times. Re-foaming is performed over a total of 6 seconds to 20 minutes, preferably 10 seconds to 5 minutes.

7) Discharge a suitable amount of foam on a brush, and apply the foam to a part of the head hair. Repeat this operation to apply the foam over the whole head, and perform one operation of re-foaming over the whole head using the same brush over 3 seconds to 10 minutes, preferably 5 seconds to 5 minutes.

8) Discharge a suitable amount of foam on a brush, apply the foam to a part of the head hair, and perform one operation of re-foaming using the same brush or hands over 3 seconds to 10 minutes, preferably 5 seconds to 3 minutes. Repeat this operation to apply the foam over the whole head. After completion of application to the whole head, perform one operation of re-foaming using the same brush or hands over 3 seconds to 10 minutes, preferably seconds to 5 minutes.

The area for re-foaming may be the whole head hair or only a specific portion. Since foam may be thoroughly spread by performing re-foaming over the whole head hair, incomplete dyeing may be prevented even if application of foam is missed at a site that may be hardly checked, such as the hair in back of the head. In partial dyeing, when re-foaming is performed on only a specific portion, the border of a dyed portion may be made unclear, and natural finishing is provided. Furthermore, when re-foaming is performed, it is very easy to visually check portions where foam has spread. Therefore, incomplete dyeing of a portion that needs dyeing may be avoided.

After completion of the foam application, the hair is washed after the foam is left for about 3 to 60 minutes, preferably about 5 to 45 minutes. In the present invention, the above-mentioned time after completion of the foam application means all the required time from completion of application of all the foam to the whole head or a desired portion to rinsing out, and is a concept including time required for re-foaming in addition to the time for simply leaving the hair. Then, the hair is suitably washed with a shampoo or treated with a conditioner, then rinsed with water, and dried.

[Two-Part Hair Dye Composition]

The two-part hair dye composition used in the present invention contains an alkali agent in a first part, hydrogen peroxide in a second part, and (A) a surfactant in at least one of the first part and the second part. Further, (B) a higher alcohol or (C) a nonvolatile hydrophilic solvent is preferably contained in the mixture solution of the first part and the second part.

[Alkali Agent]

Examples of the alkali agent contained in the first part include ammonia, alkanolamine such as ethanolamine, sodium hydroxide, and potassium hydroxide. Furthermore, ammonium salt such as ammonium hydrogen carbonate and ammonium chloride, carbonate such as potassium carbonate and sodium hydrogencarbonate, and the like may be suitably added as buffer.

pH of the mixture solution of the first part and the second part in the two-part hair dye composition used in the present invention is preferably 8 to 11, more preferably 9 to 11, and the amount of the alkali agent used is suitably adjusted so that the mixture solution should have the above-mentioned pH.

[Hydrogen Peroxide]

The content of hydrogen peroxide in the second part is preferably 1 to 9% by mass, more preferably 3 to 6% by mass. The content of hydrogen peroxide in the mixture solution of the first part and the second part is preferably 1 to 6% by mass, more preferably 2 to 5% by mass. Further, the pH of the second part is preferably 2 to 6, more preferably pH 2.5 to 4, to prevent degradation of hydrogen peroxide.

[(A): Surfactant]

A surfactant is added to either the first part or the second part, or both parts, so that foam should be easily formed by mixing the mixture solution of the two-part hair dye with air by a foam discharging means of a foamer container, and that the foam should be stable. anionic surfactant and/or a nonionic surfactant is preferably used so that favorable foam that is readily applied to the head hair can be provided even when a solution temperature is low or close to ordinary temperature.

Examples of the anionic surfactant include, such as, a sulfuric acid ester type, sulfonic acid type, carboxylic acid type and phosphate ester type anionic surfactants. Preferred examples thereof include alkylsulfate and polyoxyalkylene alkylsulfate of the sulfuric acid ester type, with an alkyl group having 10 to 24 carbon atoms, more preferably 12 to 18 carbon atoms. Furthermore, this alkyl group is preferably linear. Furthermore, of the polyoxyalkylene alkylsulfate, polyoxyethylene alkylsulfate is more preferred. Of these, those with an oxyethylene group having an average number of additional moles of 1 to 10, more preferably 2 to 5 are preferred.

Examples of the nonionic surfactant include polyoxyalkylene alkyl ether, polyoxyalkylene alkenyl ether, polyoxyalkylene fatty acid ester, alkylglyceryl ether, polyglycerine fatty acid ester, fatty acid alkanol amide, sugar ether type, sugar ester type, and sugar amide type. Preferred examples thereof include alkyl polyglycoside, polyoxyalkylene alkyl ether and alkylglyceryl ethers. Alkyl polyglycoside preferably include an alkyl group having 8 to 18 carbon atoms, more preferably 8 to 14, even more preferably 9 to 11, and this alkyl group is preferably linear. The average degree of polymerization of a glucoside is preferably 1 to 5, more preferably 1 to 2. Polyoxyalkylene alkyl ether is preferably an ether having an alkyl group having 10 to 22 carbon atoms, more preferably 12 to 18, and this alkyl group is preferably linear. Furthermore, polyoxyethylene alkyl ethers are more preferred, and of these, the average added number of oxyethylene group is 1 to 40, more preferably 4 to 30. Alkylglyceryl ethers preferably include an alkyl group having 8 to 18 carbon atoms, more preferably 8 to 12, and this alkyl group is preferably branched.

Two or more types of component (A) may be used in combination, and the content thereof in the mixture solution of the first part and the second part is preferably 1 to 15% by mass, more preferably 2 to 10% by mass, even more preferably 2.5 to 7% by mass, even more preferably 3 to 5% by mass.

Furthermore, to improve the discharged foam quality at a low solution temperature and prevent dripping, it is preferable to use an anionic surfactant and a nonionic surfactant in combination, and the mass ratio of the anionic surfactant to the nonionic surfactant in the mixture solution (content of anionic surfactant/content of nonionic surfactant) is preferably 0.01 to 1, more preferably 0.1 to 0.5.

When the two-part hair dye composition used in the present invention is used for dyeing of the head hair, an oxidative dye or a direct dye is added to the first part. To solubilize these dyes, it is preferable to mainly use nonionic surfactant as surfactant added to the first part, taking into account the high ionic strength of ammonia and carbonates contained in the first part. On the other hand, anionic surfactants are preferably added to the second part due to the high ionic strength of the first part.

[(B): Higher Alcohol]

The higher alcohol as component (B) is used to allow foam to be maintained longer and to improve the effect of preventing dripping during the foam being left to develop after application of a two-part hair dye composition to the head hair. Higher alcohols preferably include an alkyl or alkenyl group having 10 to 30 carbon atoms, more preferably 12 to 24 carbon atoms, even more preferably 14 to 22. Of these, those including an alkyl group, more preferably a linear alkyl group are preferred. Examples of the higher alcohol as component (B) include myristyl alcohol, cetanol, stearyl alcohol, behenyl alcohol, isostearyl alcohol, and oleyl alcohol. Two or more thereof may be used in combination.

Two or more types of component (B) may be used in combination, and may be added to either the first part or the second part or both parts. The content of component (B) in the mixture solution of the first part and the second part is preferably 0.05 to 1% by mass, more preferably 0.1 to 0.8% by mass, even more preferably 0.2 to 0.6% by mass, even more preferably 0.3 to 0.4% by mass from viewpoints that foaming property is not deteriorated at a low solution temperature, and that the effect of preventing dripping during the foam being left to develop is improved.

In the present invention, the mass ratio of component (B) to component (A) in the mixture solution (content of component [B]/content of component [A]) is preferably 0.02 to 0.4, preferably 0.03 to 0.3, more preferably 0.05 to 0.2 to improve the foam quality at a low solution temperature and prevent dripping.

[(C): Nonvolatile Hydrophilic Solvent]

Furthermore, it is preferable to add (C) a nonvolatile hydrophilic solvent to the first part or the second part. Consequently, irritation on the scalp may be reduced which occurs because water is evaporated from the two-part hair dye composition while leaving to develop after application of the two-part hair dye composition to the head hair, and therefore irritating components such as hydrogen peroxide are concentrated. Preferred examples of the nonvolatile hydrophilic solvent include substances without a defoaming action such as polyols and lower alkyl ethers (having 1 to 4 carbon atoms) derived therefrom. Polyols having 2 to 6 carbon atoms are preferred, and examples thereof include glycerin, diglycerin, propylene glycol, dipropylene glycol, 1,3-butane diol, ethylene glycol, diethylene glycol, isoprene glycol, and sorbitol. Examples of lower alkyl ether derived from polyol include mono-lower alkyl ethers and poly-lower alkyl ethers derived from the above-mentioned polyols (e.g., di-lower alkyl ether). Of these, mono-methyl ether and mono-ethyl ether derived from polyols are preferred, and specific examples thereof include ethylene glycol mono-methyl ether, ethylene glycol mono-ethyl ether, diethylene glycol mono-methyl ether, and diethylene glycol mono-ethyl ether. Two or more thereof may be used in combination.

The content of the nonvolatile hydrophilic solvent in the mixture solution of the first part and the second part is preferably 0.1 to 4% by mass, more preferably 0.5 to 3% by mass, even more preferably 1 to 2% by mass, from viewpoints that irritation of the scalp is reduced, and that favorable foam quality is maintained even at a low solution temperature.

Not to cause irritation to the scalp even when the content of the nonvolatile hydrophilic solvent is reduced and to maintain a hair dyeing ability and a bleaching ability, the mass ratio of component (A) to component (C) (content of component [A]/content of component [C]) is preferably 1 to 20, more preferably 1 to 10, even more preferably 1.5 to 5, even more preferably 2 to 4.

[(D): Polyquaternium-7]

Polyquaternium-7 as component (D) may be further added to the two-part hair dye composition used in the present invention to improve the effect of preventing dripping. As component (D), commercially available products such as, for example, Merquat 550 (Nalco) may be used.

The content of component (D) in the mixture solution of the first part and the second part is preferably 0.01 to 3% by mass, more preferably 0.1 to 1% by mass, even more preferably 0.2 to 0.5% by mass to realize favorable foam that is easily applied to the head hair even when the solution temperature is low or close to ordinary temperature, and to obtain an effect of preventing the mixture solution from dripping down between the time of application to the hair and the time of rinsing out.

[(E): Polyquaternium-22]

Polyquaternium-22 as component (E) may be further added to the two-part hair dye composition used in the present invention to control the defoaming property after application to the hair, maintain adequate residual foam, and easily check applied sites. As component (E), commercially available products such as, for example, Merquat 280 and Merquat 295 (both produced by Nalco) may be used.

The content of component (E) in the mixture solution of the first part and the second part is preferably 0.01 to 0.5% by mass, more preferably 0.1 to 0.2% by mass to obtain the above-described effects without deteriorating the foaming property at a low solution temperature.

[Dyes]

The two-part hair dye composition of the present invention may be used for bleaching of the head hair when a dye is not added to the mixture solution of the first part and the second part, and also may be used for hair dyeing by adding an oxidative dye or a direct dye. When the composition is used for hair dyeing, the first part contains an oxidative dye and/or a direct dye. Examples of the oxidative dye include dye precursors such as p-phenylenediamine, toluene-2,5-diamine, o-chlor-p-phenylenediamine, N-phenyl-p-phenylenediamine, N,N-bis(hydroxyethyl)-p-phenylenediamine, 3-methyl-4-aminophenol, 2-hydroxyethyl-p-phenylenediamine, p-aminophenol, p-methylaminophenol, 4-amino-m-cresol, o-aminophenol, 1-hydroxyethyl-4,5-diaminopyrazole, and salts thereof; and couplers such as resorcin, 2-methylresorcin, 1-naphthol, 1,5-dihydroxynaphthalene, 5-amino-o-cresol, m-phenylenediamine, m-aminophenol, 2,4-diaminophenoxyethanol, 2,6-diaminopyridine, 2-methyl-5-hydroxyethylaminophenol, 2-amino-3-hydroxypyridine, and salts thereof.

Examples of the direct dye include basic dyes, nitro dyes, dispersive dyes, and cationic dyes. More specific examples thereof include 2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, N,N-bis(2-hydroxyethyl)-2-nitro-p-phenylenediamine, Dispersive Purple 1, Dispersive Blue 1, Dispersive Black 9, Basic Blue 99, Basic Brown 16, Basic Brown 17, Basic Red 76, Basic Yellow 76, Basic Orange 31, Basic Red 51, and so forth.

[Silicones]

It is preferable that silicone is not added to the mixture solution of the first part and the second part in the two-part hair dye composition used in the present invention from a viewpoint that discharged foam may be maintained for a long time, however, silicone may be added to a certain extent to work the foam into the head hair smoothly and exert a high conditioning effect on the head hair. Examples of the silicones include dimethylpolysiloxane, methylphenylpolysiloxane, polyether-modified silicone, amino-modified silicone, and oxazoline-modified silicone elastomer, and emulsion obtained by dispersing these silicones in water using surfactants. Of these, polyether-modified silicone, amino-modified silicone, and emulsion thereof are preferred, from a viewpoint that a stable dispersion in water is enabled without using a thickening agent.

When silicones are used for the above-described purpose, the content of the silicones in the mixture solution of the first part and the second part is preferably 0.01 to 0.5% by mass, more preferably 0.02 to 0.4% by mass, even more preferably 0.05 to 0.3% by mass.

[Other Components]

In addition, depending on the purposes, fragrance, ultraviolet absorber, metal sequestering agent such as edetic acid, disinfectant, preservative such as methyl paraoxybenzoate, stabilizer such as fenasetin, etidronic acid, and oxyquinoline sulfate, organic solvent such as ethanol, benzyl alcohol, and benzyloxyethanol, water-soluble polymer such as Polyquaternium-6, Polyquaternium-39, and hydroxyethylcellulose, moisturizing agent and the like may be added to the first part and the second part. Furthermore, using water as the main medium in the mixture solution of the first part and second part is preferable.

[Viscosity]

The viscosity of the first part (25° C.) is preferably 1 to 50 mPa·s, more preferably 3 to 40 mPa·s, even more preferably 5 to 30 mPa·s. The viscosity of the second part (25° C.) is preferably 1 to 300 mPa·s, more preferably 3 to 200 mPa·s, even more preferably 5 to 100 mPa·s. The viscosity of the mixture solution of the first part and the second part (25° C.) is 1 to 100 mPa·s, preferably 3 to 50 mPa·s, more preferably 5 to 30 mPa·s. The value of viscosity is defined as a value obtained after rotating Rotor No. 1 of Type B Rotational Viscometer (model TV-10) produced by Tokimec Inc. for 1 minute. Measurement is performed at 60 rpm for 100 mPa·s or lower, 30 rpm for 100 to 200 mPa·s, and 12 rpm for 200 to 500 mPa·s. By adjusting the viscosity of the mixture solution within the above-mentioned range, the mixture solution may be mixed uniformly without foaming and easily applied to the head hair, foam is well worked into the head hair, and uniform foam that hardly drips after application to the head hair may be obtained.

By adjusting the viscosity within the above-mentioned range, quality of foam that may be easily applied to and worked into the head hair may be provided, foam may be prevented from dripping down after application to the head hair, and foam may be easily discharged using a non-aerosol type foamer. In order to adjust viscosity to fall within the above-mentioned range, water-soluble solvents such as ethanol may be added, or contents and types of surfactant, polyols, higher alcohol, and the like may be suitably adjusted.

[Gas-Liquid Mixing Ratio]

The gas-liquid mixing ratio of air as foam discharged using a foamer container to the mixture solution is preferably 10 to 50 mL/g, more preferably 15 to 40 mL/g, even more preferably 20 to 30 mL/g, from viewpoints that the compositions may be easily applied to and worked into the head hair. It is noted that the gas-liquid mixing ratio here is a value measured as follows.

The gas-liquid mixing ratio is determined by measuring the mass and the volume of foam discharged at 25° C. are measured. 100 g of the mixture solution is placed in a foamer container, 20 g of foam is discharged into a 1000 mL, measuring cylinder, the volume of the foam is measured at 1 minute after the start of discharge. The gas-liquid mixing ratio (mL/g) is obtained by dividing the volume (mL) of this discharged foam by 20 g, the mass thereof.

EXAMPLES

Example 1, Comparative Example 1

A first part and a second part of a two-part hair dyeing composition having the composition shown in Table 1 are prepared. As shown in FIG. 1, 40 g of a first part (A1) is filled in a first container (2) and 60 g of a second part (A2) in a second container (3) (which also serves as a squeeze container main body (4); internal volume, 210 mL). Further, a squeeze foamer (5) (SI Squeeze Foamer produced by Daiwa Can Company) is also prepared.

TABLE 1

| First part | Content in first part (% by mass) |
|---|---|
| Para-aminophenol | 0.8 |
| Meta-aminophenol | 0.2 |
| Toluene-2,5-diamine | 0.5 |

TABLE 1-continued

| | |
|---|---|
| Resorcin | 0.6 |
| Aqueous ammonia (25% by mass) | 8.5 |
| Ammonium hydrogen carbonate | 8.0 |
| Decylglucoside | 3.2 |
| Laureth-23 | 2.0 |
| Propylene glycol | 4.0 |
| Polyquaternium-22 | 0.4 |
| Methylparaben | 0.1 |
| EDTA-4Na | 0.5 |
| Fragrance | 0.3 |
| Ascorbic acid | 0.4 |
| Anhydrous sodium sulfite | Balance |
| Water | |

| Second part | Content in second part (% by mass) |
|---|---|
| Sodium laureth sulfate | 1.9 |
| Lauramide propyl betaine | 0.05 |
| Lauryl hydroxysultaine | 0.05 |
| Lauric acid | 0.04 |
| Cetanol | 1.5 |
| Etidronic acid | 0.04 |
| Phosphoric acid (75% by mass) | Amount required to adjust pH to 3.8 |
| Sodium hydroxide solution (48% by mass) | 0.01 |
| Oxyquinoline sulfate | 0.04 |
| Glycerine | 5.0 |
| Aqueous hydrogen peroxide (35% by mass) | 16.3 |
| Water | Balance |

Subjects (Japanese females with a gray hair percentage of 30%: the hair is cut at a length aligned to the jaw line) receive the above-mentioned filled first part and second part and the squeeze foamer, and perform hair dyeing by the following procedure. The applied hair dye is compared between when an operation of re-foaming on the head hair is performed (Example 1) and when this operation is not performed (Comparative Example 1) in a half-head study. Evaluation results are shown later.

Figure 2:
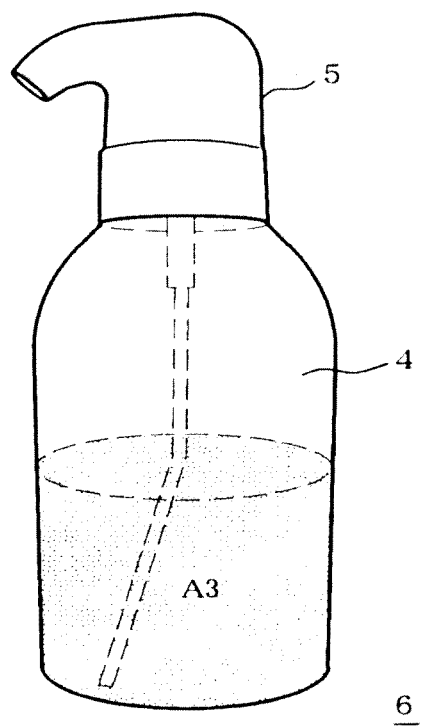
FIG. 2 shows a state of the two-part hair dye composition used in the examples and the comparative examples after mixing.

Hair Dyeing Procedure 1. 40 g of a first part is placed in a container main body (4) of a squeeze container containing 60 g of a second part and mixed, so that the mixture solution of the first part and the second part should not foam, then a squeeze foamer (5) is mounted (FIG. 2).

2. Gloves are put on, the squeeze container is squeezed with one hand in an upright position, and the mixture solution as foam is discharged on the other hand.

3. The mixture solution as foam is applied to the dry head hair.

4. The operations at steps 2 and 3 are repeated, and the total volume (100 g) of the mixture solution is applied to the whole head hair so as to be evenly distributed between the right and left sides.

5. The mixture solution applied on the right half of the head hair is re-foamed by rubbing the roots of the head hair with fingers, so that the right half of the head hair should be covered with the foam (Example 1). The left half of the head hair is left as it was (Comparative Example 1).

6. The mixture is left for 30 minutes after completion of the re-foam operation on the right half of the head hair.

7. The whole head hair is rinsed with warm water, shampooed, treated with a conditioner, and dried successively.

Evaluation Results (1) Dripping of Mixture Solution

Example 1

No dripping is observed during the 30 minutes from the start of leaving at step 6.

Comparative Example 1

Dripping occurs at the neckline at 10 minutes after the start of leaving at step 6. Thereafter, dripping also occurs around the forehead and ears.

(2) Uneven Dyeing

Example 1

The hair is evenly dyed both on the surface and at the roots.

Comparative Example 1

Although the hair on the surface is evenly dyed, the hair at the roots on the back of the head is not dyed at some sites. This appears to be because application of the mixture solution is incomplete.

Example 2

A first part and a second part of a two-part hair dyeing composition having the composition shown in Table 2 are prepared. These parts are filled in the same containers as in Example 1. Further, the same squeeze foamer as in Example 1 is prepared.

TABLE 2

| First part | Content of first part (% by mass) |
|---|---|
| Toluene-2,5-diamine | 0.14 |
| Para-aminophenol | 0.1 |
| Meta-aminophenol | 0.05 |
| Para-amino-ortho-cresol | 0.1 |
| 2,4-Diaminophenoxyethanol hydrochloride | 0.15 |
| Aqueous ammonia (28% by mass) | 6.0 |
| Ammonium hydrogen carbonate | 10.5 |
| Decylglucoside | 6.5 |
| Trideceth-9 | 0.6 |
| Laureth-23 | 1.8 |
| Myristyl alcohol | 0.2 |
| Propylene glycol | 4.0 |
| Ethanol | 9.0 |
| Polyquaternium-7 | 0.6 |
| Polyquaternium-22 | 0.4 |
| EDTA-4Na | 0.1 |
| Ascorbic acid | 0.3 |
| Anhydrous sodium sulfite | 0.4 |
| Fragrance | 0.5 |
| Water | Balance |

| Second part | Content in second part (% by mass) |
|---|---|
| Sodium laureth sulfate | 1.9 |
| Lauramide propyl betaine | 0.05 |
| Lauryl hydroxysultaine | 0.05 |
| Lauric acid | 0.04 |
| Cetanol | 1.5 |
| Etidronic acid | 0.04 |
| Phosphoric acid (75% by mass) | Amount required to adjust pH to 3.8 |
| Sodium hydroxide solution (48% by mass) | 0.01 |
| Oxyquinoline sulfate | 0.04 |
| Glycerine | 5.0 |
| Aqueous hydrogen peroxide (35% by mass) | 16.3 |
| Water | Balance |

Subjects (Japanese females with a gray hair percentage of 30%: the hair is cut at a length aligned to the jaw line) receive the above-mentioned filled first part and second part, and the squeeze foamer hair dyeing is performed by the same procedure as in Example 1, and the hair dye is evaluated for dripping and uneven dyeing.

Evaluation Results (1) Dripping of Mixture Solution

No dripping is observed during the 30 minutes from the start of leaving at step 6.

(2) Uneven Dyeing

The hair is evenly dyed both on the surface and at the roots.

Examples 3 to 7

A first part and a second part having the composition (% by mass) shown in Table 3 are prepared. As shown in FIG. 1, 40 g of a first part (A1) is filled in a first container (2), and 60 g of a second part (A2) in a second container (3) (which also serves as a squeeze container main body (4); internal volume, 210 mL). These containers are left in a refrigerator maintained at 5° C. together with a squeeze foamer (5) (SI Squeeze Foamer produced by Daiwa Can Company) for 24 hours.

Immediately after these containers are removed from the refrigerator in a room at 20° C., the first part and the second part are mixed, and a squeeze foamer is mounted on the container, which is given to subjects (Japanese 20's-age females with black hair at a medium length). Subjects are asked to squeeze the container with one hand several times in upright position it and discharge 20 g of the mixture solution into a 1000 mL measuring cylinder. The total volume (mL) of liquid and foam at 1 minute from the start of the discharge is measured. A gas-liquid mixing ratio (mL/g) is obtained by dividing this volume by 20 g, and the quality of foam discharged at a low temperature is evaluated as follows. The results are shown in the columns below the composition in Table 3.

Quality of Foam Discharged at a Low Temperature (Evaluation by Gas-Liquid Mixing Ratio)

A: 20 mL/g or more and less than 30 mL/g;
B: 15 mL/g or more and less than 20 mL/g, or 30 mL/g or more and less than 40 mL/g;
C: 10 mL/g or more and less than 15 mL/g, or 40 mL/g or more and less than 50 mL/g;
D: less than 10 mL/g, or 50 mL/g or more.

It is noted that these evaluation criteria are established from viewpoints of the volume placed on the hand and the bath ratio at the time of application to the hair.

Further, when 75 g of the mixture solution is used, and subjects dye their own head hair by the following procedure, the mixture solution is spread all over the head hair, no dripping is observed, and a uniform hair dyeing result is obtained without uneven dyeing.

"Hair dyeing procedure"

1. Gloves are put on, the squeeze container is squeezed with one hand in an upright position, and the mixture solution as foam discharged on the other hand.
2. The mixture solution as foam is applied to the dry head hair.
3. The operations at steps 1 and 2 are repeated, and 75 g of the mixture solution is applied to the whole head hair.
4. The applied mixture solution is re-foamed by rubbing the whole head hair with fingers for 20 seconds.
5. The mixture is left for 10 minutes.
6. The applied mixture solution is re-foamed by rubbing the whole head hair with fingers for 30 seconds.
7. The mixture is left for 20 minutes after completion of the re-foam operation at step 6.
8. The whole head hair is rinsed with warm water, shampooed, treated with a conditioner, and dried successively.

Further, "irritation of scalp" during the hair dyeing is evaluated by subjects according to the following criteria. The results are shown in the columns below the composition in Table 4.

Irritation of Scalp

A: Feeling no irritation
B: Feeling little irritation
C: Feeling slight, but not unbearable, irritation
D: Feeling distinct irritation Hair Dyeing Procedure 1. 40 g of a first part is placed in a container main body (4) of a squeeze container containing 60 g of a second part and mixed, so that the mixture solution of the first part and the second part should not foam, then a squeeze foamer (5) is mounted (FIG. 2).

TABLE 3

| (% by mass) | | Example 3 | 4 | 5 | 6 | 7 |
|---|---|---|---|---|---|---|
| First part | | | | | | |
| Para-aminophenol | | 0.15 | 0.15 | 0.15 | 0.15 | 0.15 |
| Para-amino-ortho-cresol | | 0.2 | 0.2 | 0.2 | 0.2 | 0.2 |
| Toluene-2,5-diamine | | 0.1 | 0.1 | 0.1 | 0.1 | 0.1 |
| Aqueous ammonia (28% by mass) | | 6.0 | 6.0 | 6.0 | 6.0 | 6.0 |
| Ammonium hydrogen carbonate | | 10.0 | 10.0 | 10.0 | 10.0 | 10.0 |
| Decylglucoside | | 8.5 | 5.1 | 18.7 | 8.5 | 8.5 |
| Propylene glycol | | 4.0 | 4.0 | 4.0 | 4.0 | 4.0 |
| EDTA-4Na | | 0.1 | 0.1 | 0.1 | 0.1 | 0.1 |
| Ascorbic acid | | 0.4 | 0.4 | 0.4 | 0.4 | 0.4 |
| Anhydrous sodium sulfite | | 0.5 | 0.5 | 0.5 | 0.5 | 0.5 |
| Water | | Balance | Balance | Balance | Balance | Balance |
| Second part | | | | | | |
| Aqueous hydrogen peroxide (35% by mass) | | 16.3 | 16.3 | 16.3 | 16.3 | 16.3 |
| Sodium laureth sulfate | | 1.0 | 0.6 | 2.2 | 1.0 | 1.0 |
| Cetanol | | 0.6 | 0.6 | 0.6 | 0.2 | 1.5 |
| Oxyquinoline sulfate | | 0.03 | 0.03 | 0.03 | 0.03 | 0.03 |
| Etidronic acid | | 0.08 | 0.08 | 0.08 | 0.08 | 0.08 |
| Sodium hydroxide | | * | * | * | * | * |
| Water | | Balance | Balance | Balance | Balance | Balance |
| Viscosity of mixture solution (first part:second part = 1:1.5) (5° C., mPa · s) | | 3 | 3 | 3 | 2 | 28 |
| (A) Surfactant in mixture solution (% by mass) | | 4.0 | 2.4 | 8.8 | 4.0 | 4.0 |
| (B) Higher alcohol in mixture solution (% by mass) | | 0.36 | 0.36 | 0.36 | 0.12 | 0.9 |
| (B)/(A) | | 0.09 | 0.15 | 0.04 | 0.03 | 0.23 |
| Evaluation | Quality of foam discharged at low temperature | A | A | A | A | B |
| | Gas-liquid mixing ratio (mL/g) | 22 | 20 | 20 | 25 | 18 |

* Amount required to adjust second part to pH 3.5

Examples 8 to 15

First parts and second parts having the compositions (% by mass) shown in Tables 4 to 6 are prepared. As shown in FIG. 1, 40 g of a first part (A1) is filled in a first container (2), and 60 g of a second part (A2) in a second container (3) (which also serves as a squeeze container main body (4), internal volume, 210 mL). Further, a squeeze foamer (5) (SI Squeeze Foamer produced by Daiwa Can Company) is prepared.

When subjects (Japanese 20's-age females with black hair at a medium length) receive the filled first part and second part and the squeeze foamer and perform hair dyeing by the following procedure, the mixture solution is spread all over the head hair, no dripping is observed, and a uniform hair dyeing result is obtained without uneven dyeing.

2. Gloves are put on, the squeeze container is squeezed with one hand in an upright position, and the mixture solution as foam is discharged on the other hand.
3. The mixture solution as foam is applied to the dry head hair.
4. The operations at steps 1 and 2 are repeated, and 80 g of the mixture solution is applied to the whole head hair.
5. The applied mixture solution is re-foamed by rubbing the whole head hair with fingers for 15 seconds.
6. The mixture is left for 10 minutes as is.
7. The applied mixture solution is re-foamed by rubbing the whole head hair with fingers for 25 seconds.
8. The mixture is left for 20 minutes after completion of the re-foam operation at step 7.
9. The whole head hair is rinsed with warm water, shampooed, treated with a conditioner, and dried successively.

TABLE 4

| (% by mass) | Example 8 | Example 9 | Example 10 |
|---|---|---|---|
| First part | | | |
| Para-aminophenol | 0.15 | 0.15 | 0.15 |
| Para-amino-ortho-cresol | 0.2 | 0.2 | 0.2 |
| Toluene-2,5-diamine | 0.1 | 0.1 | 0.1 |
| Aqueous ammonia (28% by mass) | 6.0 | 6.0 | 6.0 |
| Ammonium hydrogen carbonate | 10.0 | 10.0 | 10.0 |
| Decylglucoside | 6.0 | 6.0 | 9.0 |
| Laureth-23 | 2.0 | 2.0 | 3.0 |
| Propylene glycol | 5.0 | 5.0 | 4.0 |
| Polyquaternium-7 | 0.5 | 0.5 | 0.5 |
| EDTA-4Na | 0.1 | 0.1 | 0.1 |
| Ascorbic acid | 0.4 | 0.4 | 0.4 |
| Anhydrous sodium sulfite | 0.5 | 0.5 | 0.5 |
| Fragrance | 0.5 | 0.5 | 0.5 |
| Water | Balance | Balance | Balance |
| Second part | | | |
| Aqueous hydrogen peroxide (35% by mass) | 16.3 | 16.3 | 16.3 |
| Sodium laureth sulfate | 2.0 | 3.0 | 4.0 |
| Lauric acid | 0.01 | 0.01 | 0.01 |
| Glycerine | 0 | 2.0 | 0 |
| Etidronic acid | 0.08 | 0.08 | 0.08 |
| Sodium hydroxide | * | * | * |
| Water | Balance | Balance | Balance |
| Mixing ratio of first part and second part = 1:1.5 (mass ratio) | | | |
| (A) Surfactant in mixture solution (% by mass) | 4.4 | 5 | 7.2 |
| (C) Nonvolatile hydrophilic solvent in mixture solution (% by mass) | 2 | 3.2 | 1.6 |
| (A)/(C) | 2.2 | 1.6 | 4.5 |
| Evaluation — Irritation of scalp | B | B | B |

* Amount required to adjust second part to pH 3.5

TABLE 5

| (% by mass) | Example 11 | Example 12 |
|---|---|---|
| First part | | |
| Toluene-2,5-diamine | 0.3 | 0.3 |
| Meta-aminophenol | 0.25 | 0.25 |
| 2,4-Diaminophenoxyethanol hydrochloride | 0.05 | 0.05 |
| Aqueous ammonia (28% by mass) | 5.0 | 5.0 |
| Ammonium hydrogen carbonate | 10.0 | 10.0 |
| Decylglucoside | 6.0 | 8.0 |
| Laureth-23 | 2.0 | 2.5 |
| Propylene glycol | 4.0 | 3.5 |
| Ethanol | 7.0 | 7.0 |
| Polyquaternium-7 | 0.6 | 0.6 |
| Polyquaternium-22 | 0.4 | 0.4 |
| EDTA-4Na | 0.1 | 0.1 |
| Ascorbic acid | 0.4 | 0.4 |
| Anhydrous sodium sulfite | 0.5 | 0.5 |
| Fragrance | 0.5 | 0.5 |
| Water | Balance | Balance |
| Second part | | |
| Aqueous hydrogen peroxide (35% by mass) | 16.3 | 16.3 |
| Sodium laureth sulfate | 0.8 | 1.8 |
| Lauramide propyl betaine | 0.03 | 0.08 |
| Lauryl hydroxysultaine | 0.02 | 0.08 |
| Octoxyglycerine | 0.05 | 0.05 |
| Cetanol | 0.5 | 0.5 |
| Stearyl alcohol | 0.2 | 0.2 |
| Lauric acid | 0.02 | 0.02 |
| Etidronic acid | 0.08 | 0.08 |
| Sodium hydroxide | * | * |
| Water | Balance | Balance |
| Mixing ratio of first part and second part = 1:1.5 (mass ratio) | | |
| (A) Surfactant in mixture solution (% by mass) | 3.74 | 5.406 |
| (C) Nonvolatile hydrophilic solvent in mixture solution (% by mass) | 1.6 | 1.4 |
| (A)/(C) | 2.3 | 3.9 |
| Evaluation — Irritation of scalp | A | A |

* Amount required to adjust second part to pH 3.5

TABLE 6

| (% by mass) | Example 13 | Example 14 | Example 15 |
|---|---|---|---|
| First part | | | |
| Toluene-2,5-diamine | 1.6 | 1.6 | 1.6 |
| Meta-aminophenol | 0.2 | 0.2 | 0.2 |
| Resorcin | 1.0 | 1.0 | 1.0 |
| 2,4-Diaminophenoxyethanol hydrochloride | 0.5 | 0.5 | 0.5 |
| Aqueous ammonia (28% by mass) | 3.0 | 3.0 | 3.0 |
| Ammonium hydrogen carbonate | 2.5 | 2.5 | 2.5 |
| Decylglucoside | 8.0 | 8.0 | 8.0 |
| Trideceth-9 | 1.0 | 1.0 | 1.0 |
| Laureth-23 | 2.0 | 2.0 | 2.0 |
| Sodium laureth sulfate | 1.5 | 1.5 | 1.5 |
| Lauramide propyl betaine | 0.01 | 0.01 | 0.35 |
| Myristyl alcohol | 0.1 | 0.1 | 0.1 |
| Propylene glycol | 1.0 | 2.0 | 10.0 |
| Ethanol | 10.0 | 10.0 | 5.0 |
| Polyquaternium-7 | 0.6 | 0.6 | 0.6 |
| Polyquaternium-22 | 0.4 | 0.4 | 0.4 |
| EDTA-4Na | 0.1 | 0.1 | 0.1 |
| Ascorbic acid | 0.3 | 0.3 | 0.3 |
| Anhydrous sodium sulfite | 0.4 | 0.4 | 0.4 |
| Fragrance | 0.5 | 0.5 | 0.5 |
| Water | Balance | Balance | Balance |
| Second part (common) | | | |
| Aqueous hydrogen peroxide (35% by mass) | 16.3 | 16.3 | 16.3 |
| Sodium laureth sulfate | 2.5 | 2.5 | 0.4 |
| Octoxyglycerine | 0.1 | 0.1 | 0.1 |
| Lauryl hydroxysultaine | 0.01 | 0.01 | 0.1 |
| Cetanol | 0.35 | 0.35 | 0.35 |
| Stearyl alcohol | 0.15 | 0.15 | 0.15 |
| Oxyquinoline sulfate | 0.04 | 0.04 | 0.04 |
| Etidronic acid | 0.08 | 0.08 | 0.08 |
| Sodium hydroxide | * | * | * |
| Water | Balance | Balance | Balance |
| Mixing ratio of first part and second part = 1:1.5 (mass ratio) | | | |
| (A) Surfactant in mixture solution (% by mass) | 6.57 | 5.67 | 5.5 |
| (C) Nonvolatile hydrophilic solvent in mixture solution (% by mass) | 0.4 | 0.8 | 4.0 |
| (A)/(C) | 16.4 | 8.2 | 1.4 |
| Evaluation — Irritation of scalp | B | B | A |

* Amount required to adjust second part to pH 3.5

The invention claimed is:

1. A two-part hair dye comprising a first part containing an alkali agent, a second part containing hydrogen peroxide, and a non-aerosol type foamer container for discharging a mixture solution of the first part and the second part as foam, wherein the mixture solution comprises components (A) and (B), component (A) is a surfactant and is 1 to 15% by mass of the mixture solution, component (B) is a higher alcohol and is 0.05 to 1% by mass of the mixture solution and the mass ratio of component (B) to component (A) (content of component (B)/content of component (A)) is 0.02 to 0.2.

2. The two-part hair dye according to claim 1, wherein pH of the mixture solution is 8 to 11.

3. The two-part hair dye according to claim 1, wherein the viscosity of the mixture solution (25° C.) is 1 to 100 mPa·s.

4. The two-part hair dye according to claim 1, wherein the surfactant comprises at least one selected from the group consisting of an anionic surfactant and a nonionic surfactant.

5. The two-part hair dye according to claim 4, wherein the anionic surfactant comprises at least one selected from the group consisting of a sulfuric acid ester type, sulfonic acid type, carboxylic acid type and phosphate ester type anionic surfactant.

6. The two-part hair dye according to claim 5, wherein the sulfuric acid ester type anionic surfactant comprises at least one selected from the group consisting of an alkylsulfate and a polyoxyalkylene alkylsulfate.

7. The two-part hair dye according to claim 4, wherein the nonionic surfactant comprises at least one selected from the group consisting of a polyoxyalkylene alkyl ether, polyoxyalkylene alkenyl ether, polyoxyalkylene fatty acid ester, alkylglyceryl ether, polyglycerine fatty acid ester, fatty acid alkanol amide, sugar ether type, sugar ester type, and sugar amide type.

8. The two-part hair dye according to claim 1, wherein the surfactant comprises an anionic surfactant and a nonionic surfactant, wherein the mass ratio of the anionic surfactant to the nonionic surfactant in the mixture solution (content of anionic surfactant/content of nonionic surfactant) is 0.01 to 1.

9. The two-part hair dye according to claim 8, wherein the higher alcohol comprises a linear alkyl group.

10. The two-part hair dye according to claim 1, wherein the mixture solution comprises component (C) a nonvolatile hydrophilic solvent.

11. The two-part hair dye according to claim 10, wherein the component (C) comprises at least one selected from the group consisting of a polyol and a lower alkyl ether derived from the polyol.

12. The two-part hair dye according to claim 10, wherein the content of the component (C) in the mixture solution is 0.1 to 4% by mass.

13. The two-part hair dye according to claim 10, wherein the mass ratio of component (A) to component (C) (content of component (A)/content of component (C)) is 1 to 20.

14. The two-part hair dye according to claim 1, wherein the mixture solution comprises component (D) Polyquaternium-7.

15. The two-part hair dye according to claim 14, wherein the content of the component (D) in the mixture solution is 0.01 to 3% by mass.

16. The two-part hair dye according to claim 1, wherein the mixture solution comprises component (E) Polyquaternium-22.

17. The two-part hair dye according to claim 16, wherein the content of the component (E) in the mixture solution is 0.01 to 0.5% by mass.

18. The two-part hair dye according to claim 1, wherein the higher alcohol comprises an alkyl or alkenyl group having 10 to 30 carbon atoms.

* * * * *